(12) United States Patent
McKelvey et al.

(10) Patent No.: US 6,589,517 B1
(45) Date of Patent: Jul. 8, 2003

(54) HAIR CARE COMPOSITIONS

(75) Inventors: Graham Neil McKelvey, Woking (GB); Kareine Rigal, Egham (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/088,010

(22) PCT Filed: Sep. 15, 2000

(86) PCT No.: PCT/IB00/01313
§ 371 (c)(1), (2), (4) Date: Mar. 13, 2002

(87) PCT Pub. No.: WO01/22928
PCT Pub. Date: Apr. 5, 2001

(30) Foreign Application Priority Data

Sep. 30, 1999  (EP) .............................................. 99870197

(51) Int. Cl.[7] .......................... A61K 7/06; A61K 7/075; A61K 7/08; A61K 31/74; A61K 7/00
(52) U.S. Cl. ................ 424/70.1; 424/70.27; 424/78.02; 424/78.08; 424/400; 424/401
(58) Field of Search .............................. 424/70.1, 78.02, 424/78.08, 400, 401, 70.27

(56) References Cited

U.S. PATENT DOCUMENTS

| 5,100,657 A | * | 3/1992 | Ansher-Jackeson et al. ...................... 424/70.1 |
| 5,277,899 A | | 1/1994 | McCall |

FOREIGN PATENT DOCUMENTS

| EP | 0 824 914 A1 | 2/1998 |
| EP | 0 875 557 A2 | 11/1998 |
| WO | WO-95/03781 A1 | 2/1995 |
| WO | WO-98/09608 A2 | 3/1998 |
| WO | WO-99/49836 A1 | 10/1999 |

* cited by examiner

Primary Examiner—Shelley A. Dodson
(74) Attorney, Agent, or Firm—Linda M. Sivik; Tara M. Rosnell

(57) ABSTRACT

According to the present invention there is provided hair treatment compositions comprising: (a) at least one associative polymer; (b) at least one long chain alcohol; (c) at least one cationic surfactant; wherein the weight ratio of (b):(c) is greater about 1.5:1. The compositions of the present invention have an excellent rheology profile and deliver good conditioning benefits. The compositions herein are stable during storage white being easy to dispense and apply to the hair.

11 Claims, No Drawings

HAIR CARE COMPOSITIONS

This application is a 371 of PCT/IB00/01313 filed Sep. 15, 2000,

The present invention relates to hair care compositions. In particular, it relates to hair care compositions which give good conditioning and have good viscosity characteristics.

BACKGROUND TO THE INVENTION

Hair is often subjected to a wide variety of insults that can cause damage. These include shampooing, rinsing, drying, heating, combing, styling, perming, colouring, exposure to the elements etc. Thus the hair is often in a dry, rough, lusterless or frizzy condition due to abrasion of the hair surface and removal of the hair's natural oils and other natural conditioning and moisturizing components.

A variety of approaches have been developed to alleviate these conditions. These include the use of ultra mild shampoo compositions, the use of hair conditioning shampoos which attempt to both cleanse and condition the hair from a single product and the use of hair conditioning formulations such as rinse-off and leave-on products. Leave-on hair care formulations provide added advantages over the other approaches. For example, leave-on formulations are more cost effective and work for a longer duration because the conditioning ingredients remain on the hair. They are more convenient because the consumer can use the product at any time and does not have to wait to rinse the product.

Also, the product may be applied to the parts of the hair most in need of the conditioning benefits.

Commonly, the conditioning benefit is provided through the use of hair conditioning agents such as cationic surfactants, cationic polymers, silicone conditioning agents, hydrocarbon and other organic oils and solid aliphatics such as fatty alcohols. These conditioning agents are well known in the art. See, for example, WO-A-97/35542, WO-A-97/35545, WO-A-97/35546, all of which describe the use of conditioning agents in shampoo compositions, GB-A-2,211,192, which describes the use of cationic polysaccharides in a rinse-off conditioning composition and DE-A-4,326,866 which describes a composition for use prior to cutting of the hair that comprises a cationic polysaccharide. For optimal effect the conditioning agent should be evenly distributed through the hair. It is therefore important, especially for leave-on compositions, that the rheology profile be such that the composition is easy to dispense, easy to apply to the hair and easy to work through the hair. However, it can be difficult to formulate compositions that have an excellent rheology profile as well as good conditioning benefits. This problem has been addressed in a number of ways. For example, US-A-5,100,657, US-A-5,104,646 and US-A-5,106,609 all disclose hair conditioning compositions that are based on a substantially non-depositing vehicle base.

It has now been surprisingly found that compositions comprising at least one associative polymer, at least one long chain aliphatic alcohol and at least one cationic surfactant, wherein the weight ratio of alcohol to surfactant is greater than about 1.5:1, have excellent rheology profiles while at the same time provide good conditioning benefits to the hair.

While not wishing to be bound by theory, it is believed that the associative polymers form a 'gel-like' network with the cationic surfactant and the long chain alcohol. This interaction is thought to be strong enough to provide stability during storage and dispensing while at the same time being weak enough to break down under the shear stresses associated with application to the hair thereby providing a product which is easy to work through the hair.

SUMMARY OF THE INVENTION

According to the present invention there is provided hair care compositions comprising:
(a) at least one associative polymer;
(b) at least one long chain aliphatic alcohol;
(c) at least one cationic surfactant;
wherein the weight ratio of (b):(c) is greater than about 1.5:1.

The compositions of the present invention have an excellent rheology profile and deliver good conditioning benefits. The compositions herein are stable during storage while being easy to dispense and apply to the hair.

All percentages herein are by weight of the composition unless otherwise indicated. All ratios are weight ratios unless otherwise indicated. Unless otherwise indicated, all percentages, ratios, and levels of ingredients referred to herein are based on the actual amount of the ingredient, and do not include solvents, fillers, or other materials which may be combined with the ingredient in commercially available products.

All documents referred to herein, including all patents, all patent applications and all articles, are hereby incorporated herein by reference in their entirety unless otherwise indicated.

As used herein the term "leave-on" means a hair care composition that is intended to be used without a rinsing step. Therefore, leave-on compositions will generally be left on the hair until the consumer next washes their hair as part of their cleansing regimen. Leave-on will generally comprise less than about 5% of anionic surfactant.

DETAILED DESCRIPTION OF THE INVENTION

The hair care compositions of the present invention comprise at least one associative polymer, at least one cationic surfactant and at least one long chain alcohol. The weight ratio of long chain alcohol to cationic surfactant is greater than about 1.5:1, preferably at least about 2:1, more preferably at least about 2.5:1, even more preferably at least about 3:1, still more preferably about 4:1.

Preferably, the compositions of the present invention are leave-on compositions.

Assocaitive Polymers

The compositions of the present invention must comprise at least one associative polymer.

In the compositions according to the present invention preferred associative polymers are nonionic associative polymers having an average molecular weight in the range of from about 2,000 to about 2,000,000, preferably from about 10,000 to about 1,000,000, more preferably from about 20,000 to about 800,000.

Associative polymers are a subclass of water-soluble polymers and are generally water-soluble macromolecular structures having both hydrophilic and hydrophobic components. Associative polymers can thicken compositions as a result of intermolecular association between the various water-insoluble hydrophobic components which form a part of, or are bonded to (directly or indirectly) a water-soluble polymer backbone (discussed in detail by G. D. Shay in Polymers in Aqueous Media, Advances in Chemistry series 223, pp467. Edited by J. E. Glass).

Associative polymers suitable for use in the compositions of the present invention include, but are not limited to, hydrophobically modified hydroxyalkyl cellulose polymers such as hydrophobically modified hydroxyethyl cellulose (HMHEC), hydrophobically modified alkoxylated urethane polymers, such as hydrophobically modified ethoxylated urethane (HEUR), and hydrophobically modified nonionic polyols. Preferred for use herein are hydrophobically modified hydroxyalkyl cellulose polymers and hydrophobically modified alkoxylated urethane polymers and mixtures thereof. More preferred are hydrophobically modified hydroxyalkyl cellulose polymers and mixtures thereof.

Hydrophobically Modified Hydroxyalkyl Cellulose Thickener

Cellulose ethers suitable for use herein, have, prior to hydrophobic modification, a sufficient degree of nonionic substitution selected from methyl, ethyl, hydroxyethyl and hydroxypropyl to cause them to be water-soluble. The preferred degree of nonionic substitution is in the range of from about 1.8 to about 4.0, preferably from about 2 to about 3, and especially from about 2.2 to about 2.8 by weight. The cellulose ethers are then further substituted with alkyl or alkenyl groups having from about 8 to about 30, preferably from about 10 to about 24, more preferably from about 14 to about 18 carbon atoms in an amount of from about 0.1 to about 1, preferably from about 0.3 to about 0.8, and especially from about 0.4 to about 0.6 weight percent. The cellulose ether to be modified is preferably one of low to medium molecular weight, i.e., less than 800,000 and preferably between 20,000 and 700,000 (75 to 2500 D.P.). Degree of polymerisation (D.P.) as defined herein, means, the average number of glycoside units in the polymer.

Preferred cellulose ethers for use herein are selected from commercially available nonionic cellulose ethers such as hydroxy ethyl cellulose, hydroxy propyl methyl cellulose, hydroxy methyl cellulose, ethyl hydroxy ethyl cellulose and mixtures thereof.

The preferred cellulose ether substrate, for use herein, is a hydroxyethyl cellulose (HEC) of from about 50,000 to about 700,000 molecular weight. Hydroxyethyl cellulose of this molecular weight level is the most hydrophilic of the materials completed. Accordingly, control of the modification process and control of the properties of the modified product can be more precise with this substrate. Hydrophilicity of the most commonly used nonionic cellulose ethers varies in the general direction: hydroxyethyl>hydroxypropyl>hydroxypropyl methyl>methyl.

The long chain alkyl modifier, for the cellulose ether, can be attached to the cellulose ether substrate via an ether, ester or urethane linkage. The ether linkage is preferred. Although the modified cellulose ether materials are referred to as being "alkyl modified", (the term alkyl as used generally herein also includes using alkenyl) it will be recognised that except in the case where modification is effected with an alkyl halide, the modifier is not a simple long chain alkyl group. The group is actually an alphahydroxyalkyl radical in the case of an epoxide, a urethane radical in the case of an isocyanate, or an acyl radical in the case of an acid or acyl chloride. General methods for making modified cellulose ethers are taught in Landoll ('277) at column 2, lines 36–65.

Commercially available materials preferred for use herein include NATROSOL PLUS Grade 330 C (™), a hydrophobically modified hydroxyethylcellulose available from Aqualon Company, Wilmington, Delaware. This material has a $C_{16}$ alkyl substitution of from 0.4% to 0.8% by weight. The hydroxyethyl molar substitution for this material is from 3.0 to 3.7. The average molecular weight for the water-soluble cellulose prior to modification is approximately 300,000. Also suitable for use herein is NATROSOL PLUS Grade 430 CS (™)

Another material of this type is sold under the trade name NATROSOL PLUS CS Grade D-67 ™, by Aqualon Company, Wilmington, Del. This material has a $C_{16}$ substitution of from 0.50% to 0.95%, by weight. The hydroxyethyl molar substitution for this material is from 2.3 to 3.7. The average molecular weight for the water soluble cellulose prior to modification is approximately 700,000. Highly preferred for use herein is Natrosol Plus Grade 330 C.

Hydrophobically Modified Alkoxylate Urethane Thickener

Hydrophobically modified water-soluble nonionic alkoxylated urethane polymers are made by prepolymerisation of a diisocyanate with a polyol followed by end capping with primary amines or primary alcohols. The resulting molecule is usually a linear block copolymer, with internal and terminal hydrophobes but branched and cross linked polymer can also be obtained.

The polymerisation process is very complex and various resulting polymer structures can be formed as reviewed in the literature by Hulden (Colloids & Surfaces, 82, 263–277), Kaczmarski et al. (Polym. Mater. Sci. Eng., 67, 282–283), and Karunasena et al. (Polymers in aqueous media, Advances in Chemistry Series, 223, 495–525). Further details on hydrophobically modified water-soluble nonionic alkoxylated urethane polymers as thickeners are discussed in the paper titled 'Polymers in Cosmetics', presented by Rohm & Haas as part of 'The Proceedings of the 20th National Congress of the Society of Italian Cosmetic Chemists 1993' at p29.

Preferred hydrophobically modified water-soluble nonionic alkoxylated urethane polymers for use herein are described by Kaczmarski et al. as linear block copolymers (which can be obtained by a step—growth process) and can have the following general structures:

$R^2$—NHCO—NH—$R^1$[NH—CO—O—$E_n$—$CH_2CH_2$O CONH—$R^1$]$_x$—NHCO—NH—$R^2$ $R^2$—O—CONH—$R^1$[NH—CO—O—$E_n$—$CH_2CH_2$O CONH—$R^1$]$_x$—NH—CO—O—$R^2$ wherein: $E_n$ is a polyol having the general formula, $(CH_2CH_2O)_n$, n can vary from 10 to 10,000, preferably from 10 to 1,000, and more preferably from 50 to 500; $R^1$ includes straight or branched chain alkyl, alkenyl or aromatic groups containing pendant functional groups e.g. COOH; $R^2$ includes straight or branched chain alkyl, alkenyl or aromatic groups containing pendant functional groups e.g. COOH and wherein $R^2$ is preferably selected from $NH_2$ or OH and wherein x represents the degree of polymerisation.

Preferred hydrophobically modified water-soluble nonionic alkoxylated urethane polymers suitable for use herein are those sold by ISP Co. under Aculyn 44 (™) and Aculyn 46 ™, by Berol Nobel under Bermodol 2101 ™, 2130 ™ and Bermodol Pur 2100 ™ and by Servo under the name Ser-Ad-FX-100 ™.

Hydrophobically Modified Nonionic Polyols

Also suitable for use herein as thickeners are hydrophobically modified water-soluble nonionic polyols. Suitable hydrophobically modified water-soluble nonionic polyols for use herein are PEG 120 methyl glucoside dioleate (available from Amercol under the trade name Glucamate DOE 120), PEG-150 pentaerythrityl tetrastearate (available from Croda under the trade name Crothix ™, PEG-75 dioleate (available from Kessco under the trade name PEG-4000 dioleate ™ and PEG-150 distearate (available from Witco under the trade name Witconal L32 ™.

Preferably, the total level of associative polymer present in the compositions herein is from about 0.001% to about 15%, more preferably about 0.01% to about 5%, even more preferably about 0.1% to about 1%.

Cationic Surfactant

A second essential component of the present invention is that they comprise at least one cationic surfactant. Cationic surfactants useful in compositions of the present invention contain amino or quaternary ammonium moieties. Cationic surfactants among those useful herein are disclosed in the following documents: M.C. Publishing Co., McCutcheon's, *Detergents & Emulsifiers*, (North American edition 1979); Schwartz, et al.; *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983.

Among the quaternary ammonium-containing cationic surfactant materials useful herein are those of the general formula:

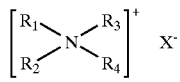

wherein $R_1$–$R_4$ are independently an aliphatic group of from about 1 to about 22 carbon atoms or an aromatic, alkoxy, polyoxyalkylene, alkylamido, hydroxyalkyl, aryl or alkylaryl group having from about 1 to about 22 carbon atoms; and X is a salt-forming anion such as those selected from halogen, (e.g. chloride, bromide), acetate, citrate, lactate, glycolate, phosphate nitrate, sulfate, and alkylsulfate radicals. The aliphatic groups may contain, in addition to carbon and hydrogen atoms, ether linkages, and other groups such as amino groups. The longer chain aliphatic groups, e.g., those of about 12 carbons, or higher, can be saturated or unsaturated. Especially preferred are mono-long chain (e.g., mono $C_{12}$ to $C_{22}$, preferably $C_{12}$ to $C_{18}$, more preferably $C_{16}$, aliphatic, preferably alkyl), di-short chain (e.g., $C_1$ to $C_3$ alkyl, preferably $C_1$ to $C_2$ alkyl) quaternary ammonium salts.

Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (with 5 moles of ethylene oxide) stearylamine, dihydroxy ethyl stearylamine, and arachidylbehenylamine. Suitable amine salts include the halogen, acetate, phosphate, nitrate, citrate, lactate, and alkyl sulfate salts. Such salts include stearylamine hydrochloride, soyamine chloride, stearylamine formate, N-tallowpropane diamine dichloride, stearamidopropyl dimethylamine citrate, cetyl trimethyl ammonium chloride and dicetyl diammonium chloride. Preferred for use in the compositions herein are cetyl trimethyl ammonium chloride, stearyl trimethyl ammonium chloride, tetradecyltrimethly ammonium chloride, dicetyldimethyl ammonium chloride, dicocodimethyl ammonium chloride and mixtures thereof. More preferred is cetyl trimethyl ammonium chloride. Cationic amine surfactants included among those useful in the present invention are disclosed in U.S. Pat. No. 4,275,055, Nachtigal, et al., issued Jun. 23, 1981.

The total level of cationic surfactants present in the compositions herein is preferably from about 0.1% to about 10%, more preferably from about 0.25% to about 5%, most preferably from about 0.3% to about 0.7%, by weight of total composition.

Long Chain Alcohols

A third essential component of the compositions of the present invention is that they comprise at least one long chain alcohol. As used herein the term "long chain alcohol" means an alcohol having eight or more carbon atoms arranged in a chain. They can be linear or branched, saturated or unsaturated. Generally the alcohols used will contain from 8 to 30 carbon atoms.

Any long chain alcohol suitable for use in hair care may be used herein. However, preferred are alcohols with $C_{10}$ to $C_{22}$ chains and mixtures thereof, more preferred are those with $C_{12}$ to $C_{20}$ chains and mixtures thereof, even more preferred are those with $C_{16}$ to $C_{18}$ chains and mixtures thereof. Preferred are alcohols with linear, saturated chains.

Preferred alcohols for use herein are those with one hydroxyl moiety (mono-ols), two hydroxyl moieties (diols) or three hydroxyl moieties (triols). More preferred are mono-ols.

Preferably the compositions of the present invention comprise a mixture of long chain alcohols. More preferred are mixtures of $C_{16}$ and $C_{18}$ long chain alcohols. Even more preferred is when the ratio of $C_{16}$ to $C_{18}$ is 3:2.

The total level of long chain alcohols present in compositions herein is preferably from about 0.1% to about 20%, more preferably from about 0.25% to about 10%, most preferably from about 0.5% to about 5%, by weight of total composition.

Optional Components

The hair care compositions of the present invention can further comprise a number of optional components. Some non-limiting examples of these optional components are given below.

Anionic Surfactant

It is preferred that the compositions of the present invention comprise less than about 10%, preferably less than about 5%, more preferably less than about 2%, even more preferably less than about 1%, even more preferably still 0%, by weight, of an anionic surfactant. As used herein, "anionic surfactant" means anionic surfactants and zwitterionic or amphoteric surfactants which have an attached group that is anionic at the pH of the composition, or a combination thereof.

Cationic Conditioningq Agents

The compositions of the present invention can also comprise one or more cationic polymer conditioning agents. The cationic polymer conditioning agents will preferably be water soluble. If present, cationic polymers preferably comprise from about 0.001% to about 20%, more typically from about 0.005% to about 10%, preferably from about 0.01% to about 2%, by weight, of the total composition.

By "water soluble cationic polymer", what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, As used herein, the term "polymer" shall include materials whether made by polymerization of one type of monomer or made by two (i.e., copolymers) or more types of monomers.

The cationic polymers hereof will generally have a weight average molecular weight which is at least about 5,000, typically at least about 10,000, and is less than about 10 million. Preferably, the molecular weight is from about 100,000 to about 2 million. The cationic polymers will generally have cationic nitrogen-containing moieties such as quaternary ammonium or cationic amino moieties, and mixtures thereof.

The cationic charge density is preferably at least about 0.1 meq/g, more preferably at least about 0.5 meq/g, even more preferably at least about 1.1 meq/g, most preferably at least about 1.5 meq/g. Generally, for practical purposes, the cationic polymers will have a cationic charge density of less than about 7 meq/g, preferably less than about 5 meq/g, more preferably less than about 3.5 meq/g, even more preferably less than about 2.5 meq/g. Cationic charge density of the cationic polymer can be determined using the Kjeldahl Method (United States Pharmacopoeia—Chemical tests—<461> Nitrogen Determination—method II). Those skilled in the art will recognise that the charge density of some amino-containing polymers may vary depending upon pH and the isoelectric point of the amino groups. The charge density should be within the above limits at the pH of intended use.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the *CTFA International Cosmetic Ingredient Dictionary and Handbook*, 7th edition, edited by Wenninger and McEwen, (The Cosmetic, Toiletry, and Fragrance Association, Inc., Washington, D.C., 1997).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the composition. In general, secondary and tertiary amines, especially tertiary amines, are preferred.

Amine-substituted vinyl monomers can be polymerised in the amine form, and then optionally can be converted to ammonium by a quaternization reaction.

Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, dialyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyidiallylammonium chloride homopolymer and copolymers of acrylamide and dimethyidiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256.

Preferred cationic polymers for use herein are cationic polymers and copolymers of saccharides. The cationic polysaccharides useful in the present invention include those polymers based on 5 or 6 carbon sugars and derivatives which have been made water-soluble by, for example, derivatising them with ethylene oxide. These polymers may be bonded via any of several arrangements, such as 1,4-α, 1,4-β, 1,3-α, 1,3-β and 1,6 linkages. The monomers may be in straight chain or branched chain geometric arrangements.

Suitable non-limiting examples of cationic polysaccharides include those based on the following: celluloses, hydroxyalkylcelluloses, starches, hydroxyalkyl starches, polymers based on arabinose monomers, polymers derived from xylose, polymers derived from fucose, polymers derived from fructose, polymers based on acid-containing sugars such as galacturonic acid and glucuronic acid, polymers based on amine sugars such as galactosamine and glucosamine particularly acetylglucosamine, polymers based on 5 or 6 membered ring polyalcohols, polymers based on galactose, polymers based on mannose monomers and polymers based on galactomannan copolymer known as guar gum.

Preferred for providing shine and conditioning benefits to the hair with reduced tack and greasiness are cationic polymers based on celluloses and acetylglucosamine derivatives, especially cationic polymers of cellulose derivatives. Non-limiting examples of suitable cationic polymers are those available from Amerchol Corp. (Edison, N.J., USA) as salts of hydroxyethyl cellulose reacted with trimethyl ammonium substituted epoxide, referred to in the industry (CTFA) as Polyquaternium 10. Background material on these polymers and their manufacture, can be found in U.S. Pat. No. 3,472,840 (issued Oct. 14 1969 to Stone), herein incorporated by reference. Other types of cationic cellulose include the polymeric quaternary ammonium salts of hydroxyethyl cellulose reacted with lauryl dimethyl ammonium-substituted epoxide, referred to in the industry (CTFA) as Polyquaternium 24, available from Amerchol Corp. (Edison, N.J., USA) and polymeric quaternary ammonium salts of hydroxyethyl cellulose reacted with diallyl dimethyl ammonium chloride, referred to in the industry (CTFA) as Polyquaternium 4, available from National Starch (Salisbury, N.C., USA).

The cationic copolymers of saccharides useful in the present invention encompass those containing the following saccharide monomers: glucose, galactose, mannose, arabinose, xylose, fucose, fructose, glucosamine, galactosamine, glucuronic acid, galacturonic acid, and 5 or 6 membered ring polyalcohols. Also included are hydroxymethyl, hydroxyethyl and hydroxypropyl derivatives of the above sugars. When saccharides are bonded to each other in the copolymers, they may be bonded via any of several arrangements, such as 1,4-α, 1,4-β, 1,3-α, 1,3-β and 1,6 linkages. Any other monomers can be used as long as the resultant polymer is suitable for use in hair care. Non-limiting examples of other monomers useful herein include dimethyidiallylammonium chloride, dimethylaminoethylmethyl acrylate, diethyldiallylammonium chloride, N,N-diallyl,N—N-dialkyl ammonium halides, and the like.

As discussed above, the cationic polymer hereof is water soluble. This does not mean, however, that it must be soluble in the composition. Preferably however, the cationic polymer is either soluble in the composition, or in a complex coacervate phase in the composition formed by the cationic polymer and anionic material. Complex coacervates of the cationic polymer can be formed with anionic surfactants or with anionic polymers that can optionally be added to the compositions hereof (e.g., sodium polystyrene sulfonate).

Silicone Conditioning Agent

The compositions of the present invention may optionally include a silicone conditioning component. The silicone conditioning component may comprise volatile silicone, nonvolatile silicone, or mixtures thereof.

The silicone conditioning component for use herein can be a silicone fluid, a silicone gum, a silicone resin and/or mixtures thereof. References disclosing non-limiting examples of some suitable silicone hair conditioning agents, and optional suspending agents for the silicone, are described in WO-A-94/08557 (Brock et al.), U.S. Pat. No. 5,756,436 (Royce et al.), U.S. Pat. No. 5,104,646 (Bolich Jr. et al.), U.S. Pat. No. 5,106,609 (Bolich Jr. et al.) and U.S. Pat. No. Reissue 34,584 (Grote et al.) British Patent 849, 433.

Silicone resins are highly cross-linked siloxane systems where the crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl, dimethyl, trimethyl, monophenyl, diphenyl, methylphenyl, ethylphenyl, propylphenyl, monovinyl, and methylvinylchlorosilanes, and tetrachlorosilane.

If present, the silicone resin will generally comprise from about 0.001% to about 10%, preferably from about 0.005% to about 5%, more preferably from about 0.01% to about 2%, even more preferably from about 0.1% to about 1%, by weight, of the total composition.

Any polysiloxane resin suitable for use in hair care compositions may be used herein including those possessing hydrogen, hydroxy, alkyl, aryl, alkoxy, alkaryl, arylalkyl arylalkoxy, alkaryloxy and alkamino substituents. However, preferred polysiloxane resins have at least one substituent group possessing delocalised electrons. This substituent can be selected from alkyl, aryl, alkoxy, alkaryl, arylalkyl arylalkoxy, alkaryloxy, and combinations thereof. Preferred are aryl, arylalkyl and alkaryl substituents. More preferred are alkaryl and arylalkyl substituents. Even more preferred are alkaryl substituents, particularly 2-phenyl propyl. Whereas it is preferred that at least one substituent have delocalised electrons, the resins herein will also generally have other substituents without delocalised electrons. Such other substituents can include hydrogen, hydroxyl, alkyl, alkoxy, amino functionalities and mixtures thereof. Preferred are alkyl substituents, especially methyl substituents.

As used herein the term "aryl" means a functionality containing one or more homocyclic or heterocyclic rings. The aryl functionalities herein can be unsubstituted or substituted and generally contain from 3 to 16 carbon atoms. Preferred aryl groups include, but are not limited to, phenyl, naphthyl, cyclopentadienyl, anthracyl, pyrene, pyridine, pyrimidine As used herein the term "alkyl" means a saturated or unsaturated, substituted or unsubstituted, straight or branched-chain, hydrocarbon having from 1 to 10 carbon atoms, preferably 1 to 4 carbon atoms. The term "alkyl" therefore includes alkenyls having from 2 to 8, preferably 2 to 4, carbons and alkynyls having from 2 to 8, preferably 2 to 4, carbons. Preferred alkyl groups include, but are not limited to, methyl, ethyl, propyl, isopropyl, and butyl. More preferred are methyl, ethyl and propyl.

As used herein the term "alkaryl" means a substituent comprising an alkyl moiety and an aryl moiety wherein the alkyl moiety is bonded to the siloxane resin.

As used herein the term "arylalkyl" means a substituent comprising an aryl moiety and an alkyl moiety wherein the aryl moiety is bonded to the siloxane resin.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', and T', denote siloxane units with one or more substituents other than methyl, and must be specifically defined for each occurrence. Therefore, the preferred polysiloxane resins for use herein have at least one M', D', or T' functionality that possesses a substituent group with delocalised electrons.

Preferred substituents are as defined hereinabove. The molar ratios of the various units, either in terms of subscripts to the symbols indicating the total number of each type of unit in the silicone (or an average thereof) or as specifically indicated ratios in combination with molecular weight complete the description of the silicone material under the MDTQ system.

Preferred polysiloxane resins for use herein are MQ and M'Q resins, more preferred are M'Q resins especially $M'_6Q_3$, $M'_8Q_4$, $M'_{10}Q_5$, $M'_{12}Q_6$ resins and mixture thereof. Preferred M'Q resins are those which have at least one group containing delocalised electrons substituted on each M' functionality. More preferred are resins where the other substituent groups are alkyl, especially methyl.

The polysiloxane resins for use herein will preferably have a viscosity of less than about 5000 $mm^2s^{-1}$, more preferably less than about 2000 $mm^2s^{-1}$, even more preferably less than about 1000 $mm^2s^{-1}$, even more still preferably less than about 600 $mm^2s^{-1}$, at 25° C. The viscosity can be measured by means of a Cannon-Fenske Routine Viscometer (ASTM D-445).

Background material on polysiloxane resins suitable for use herein, including details of their manufacture, can be found in U.S. Pat. Nos. 5,539,137; 5,672,338; 5,686,547 and 5,684,112, all of which are incorporated herein by reference.

Silicone fluids for use in the present compositions include silicone oils which are flowable silicone materials with a viscosity of less than 1,000,000 $mm^2s^{-1}$, preferably between about 5 and 1,000,000 $mm^2s^{-1}$, more preferably between about 10 and about 600,000 $mm^2s^{-1}$, more preferably between about 10 and about 500,000 $mm^2s^{-1}$, most preferably between 10 and 350,000 $mm^2s^{-1}$ at 25° C. The viscosity can be measured by means of a glass capillary viscometer as set forth in Dow Corning Corporate Test Method CTM0004, Jul. 20, 1970. Suitable silicone oils include polyalkyl siloxanes, polyaryl siloxanes, polyarylalkyl siloxanes, polyalkaryl siloxanes, polyether siloxane copolymers, and mixtures thereof. Other insoluble, nonvolatile silicone fluids having conditioning properties can also be used.

Silicone oils for use in the composition include polyalkyl or polyaryl siloxanes which conform to following formula:

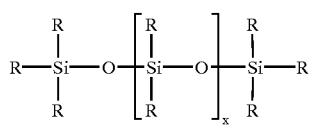

where R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure as long as the resulting silicones remain fluid at room temperature, are hydrophobic, are neither irritating, toxic nor otherwise harmful when applied to the hair, are compatible with the other components of the herein described hair care compositions, are chemically stable under normal use and storage conditions, are insoluble in the compositions of the present invention and are capable of conditioning the hair.

The two R groups on the silicon atom of each monomeric silicone unit may represent the same group or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$–$C_3$ alkyl. Examples of such polysiloxanes include polymethyl-3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified poly-dimethylsiloxane (e.g., Dow Corning DC-1248) although ethylene oxide or mixtures of ethylene oxide and propylene oxide may also be used. For insoluble silicones the ethylene oxide and polypropylene oxide level must be sufficiently low to prevent solubility in water and the composition hereof.

Other suitable silicone fluids for use in the silicone conditioning agents are insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, *Chemistry and Technology of Silicones*, New York: Academic Press 1968; and in General Electric Silicone Rubber Product Data Sheets SE 30, SE 33, SE 54 and SE 76, all of which are incorporated herein by reference. The silicone gums will typically have a mass molecular weight in excess of about 200,000, generally between about 200,000 and about 1,000,000, specific examples of which include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

The silicone conditioning agent can also comprise a mixture of polydimethylsiloxane gum (viscosity greater than about 1,000,000 centistokes) and polydimethylsiloxane oil (viscosity from about 10 to about 100,000 centistokes), wherein the ratio of gum to fluid is from about 30:70 to about 70:30, preferably from about 40:60 to about 60:40.

The number average particle size of the optional silicone component can vary widely without limitation and will depend on the formulation and/or the desired characteristics. Number average particle sizes preferred for use in the present invention will typically range from about 10 nanometres to about 100 microns, more preferably from about 30 nanometres to about 20 microns.

Background material on silicones including sections discussing silicone fluids, gums, and resins, as well as manufacture of silicones, can be found in Encyclopaedia of Polymer Science and Engineering (Volume 15, Second Edition, pp. 204–308, John Wiley & Sons, Incorporated, 1989).

A preferred silicone conditioning agent from the viewpoint of improving shine is a silicone resin.

Sensates

The hair care compositions of the present invention may also comprise a sensate. As used herein the term "sensate" means a substance that, when applied to the skin, causes a perceived sensation of a change in conditions, for example, but not limited to, heating, cooling, refreshing and the like.

Sensates are preferably utilized at levels of from about 0.001% to about 10%, more preferably from about 0.005% to about 5%, even more preferably from about 0.01% to about 1%, by weight, of the total composition.

Any sensate suitable for use in hair care compositions may be used herein. A non-limiting, exemplary list of suitable sensates can be found in GB-B-1315626, GB-B-1404596 and GB-B-1411785, all incorporated by reference herein. Preferred sensates for use in the compositions herein are camphor, menthol, l-isopulegol, ethyl menthane carboxamide and trimethyl isopropyl butanamide.

$C_1$–$C_6$ Aliphatic Alcohols

The compositions of the present invention may optionally comprise $C_1$–$C_6$, preferably $C_2$–$C_3$, more preferably $C_2$, aliphatic alcohol. The aliphatic alcohol will generally comprise from about 1% to about 75%, preferably from about 10% to about 40%, more preferably from about 15% to about 30%, even more preferably from about 18% to about 26%, by weight, of the total composition.

Alkyl Ethoxylate

The compositions of the present invention can comprise an alkyl ethoxylate. Preferred alkyl ethoxylates for use herein have the formula:

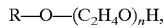
R—O—(C$_2$H$_4$O)$_n$H, wherein R is an alkyl group having from about 1 to about 30 carbon atoms, preferably from about 6 to about 22 carbon atoms, and more preferably from about 8 to about 18 carbon atoms; R may be branched, linear, saturated, unsaturated, but is preferably linear and saturated, or unsaturated having about one double bond; n is from about 1 to about 10, preferably from about 2 to about 8, and more preferably from about 3 to about 6; the weight average molecular weight of the alkyl ethoxylate is preferably less than about 500 g/mol, more preferably from about 100 to about 500 g/mol, and even more preferably from about 200 to about 500 g/mol; and the HLB value of the alkyl ethoxylate is preferably from about 5 to about 12, more preferably from about 6 to about 11, and even more preferably from about 6 to about 10.

As may be seen from the HLB values, such alkyl ethoxylates are miscible in both oil and water. Furthermore, such alkyl ethoxylates typically have a melting point of less than about 30° C., preferably less than about 25° C., and more preferably less than about 20° C., and have a cloud point (1% solution) of less than about 50° C., preferably less than about 40° C., and more preferably less than about 35° C.

Highly preferred examples of the alkyl ethoxylate useful herein include, for example, oleth-5 [$C_{18}$ (−2H)EO5] (i.e., a $C_{18}$ alkyl group having a single double bond and 5 ethoxylate groups), oleth-3 [$C_{18}$(−2H)EO3], steareth-5 ($C_{18}$EO5), steareth-4 ($C_{18}$EO4), ceteareth-5 ($C_{16}$EO5), ceteareth4 ($C_{16}$EO4), ceteareth-3 ($C_{16}$EO3), mixtures of $C_{9-11}$EO5, mixtures of $C_{9-11}$EO2.5, mixtures of $C_{12-13}$EO3, mixtures of $C_{11-13}$EO5, and mixtures thereof. These alkyl ethoxylates are available from, for example, Croda Chemical Ltd., of Parsippany, N.J., U.S.A., Shell Chemical of U.S.A., BASF of Germany, Mitsubishi Chemical of Tokyo, Japan, and Nikko Chemical, of Tokyo, Japan. Such alkyl ethoxylates are especially preferred for use in rinse-off hair conditioning compositions.

The alkyl ethoxylate is preferably present in the composition herein at a level of from about 0.1% to about 20%, more preferably from about 0.2% to about 15%, and even more preferably from about 0.5% to about 10%, by weight of the hair care composition. If the hair care composition is a rinse-off hair conditioning composition, then the alkyl ethoxylate is preferably present at a level of at least about 1%, more preferably from about 2% to about 20%, and even more preferably from about 3%. to about 10%, by weight of the rinse-off hair conditioning composition.

If the hair care composition is intended for use as a rinse-off hair conditioning composition, it is highly preferred that the alkyl ethoxylate have a cloud point of less than about 40° C. Without intending to be limited by theory, it is believed that this significantly improves the deposition efficiency of the alkyl ethoxylate onto hair.

PolyproDylene Glycol

The compositions of the present invention can also comprise a polypropylene glycol. Preferably the polypropylene glycol is selected from a single-polypropylene glycol-chain segment polymer of Formula I, below, a multi-polypropylene glycol-chain segment polymer of Formula II, below, and mixtures thereof.

The polypropylene glycols useful herein are typically polydisperse polymers. Prefebably, the polypropylene glycols useful herein have a polydispersity of from about 1 to about 2.5, more preferably from about 1 to about 2, and even more preferably from about 1 to about 1.5. As used herein, the term "polydispersity" indicates the degree of the molecular weight distribution of the polymer sample. Specifically, the polydispersity is a ratio, greater than 1, equal to the weight average molecular weight divided by the number average molecular weight. For a further discussion about polydispersity, see "Principles of Polymerization," pp. 20–24, G. Odian, (John Wiley & Sons, Inc., 3$^{rd}$ ed., 1991).

If present, the polypropylene glycol typically comprises from about 0.5% to about 10%, and preferably from about 2% to about 6%, by weight, of the total composition.

Single-Polypropylene Glycol-Chain Segment Polymer

The single-polypropylene glycol-chain segment polymer useful herein has the formula:

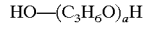
HO—(C$_3$H$_6$O)$_a$H        (Formula I), wherein a is a value from about 20 to about 100, and preferably from about 20 to about 40, and more preferably from about 20 to about 30. Although it is dependent upon the polydispersity of the actual single-polypropylene glycol-chain segment polymer preparation, such a preparation typically has a weight average molecular weight of from about 2,000 to about 10,000 g/mol, preferably of from about 3,000 to about 8,000 g/mol.

In a preferred embodiment, one or more of the propylene repeating groups in the polypropylene glycol is an isopropyl oxide repeating group. More preferably, substantially all of the propylene oxide repeating groups of the polypropylene glycol of Formula I are isopropyl oxide repeating groups. Accordingly, a highly preferred single-polypropylene glycol-chain segment polymer has the formula:

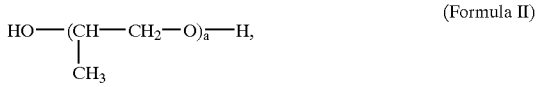
(Formula II)

wherein a is defined as described above for Formula I.

In a preferred embodiment, one or more of the propylene repeating groups in the polypropylene glycol is an isopropyl oxide repeating group. More preferably substantially all of the propylene oxide repeating groups of the polypropylene glycol of Formula II are isopropyl oxide repeating groups. Accordingly, a highly preferred multi-polypropylene glycol-chain segment polymer has the formula:

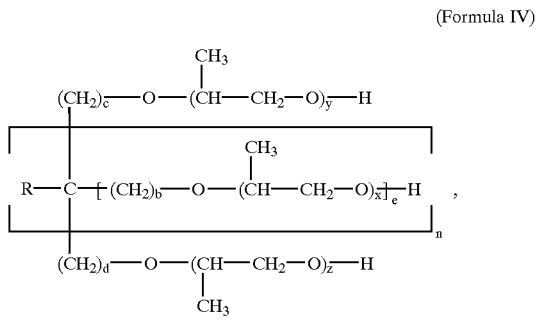
(Formula IV)

wherein n, R, b, c, d, e, x, y, and z are defined as above, for Formula III. It is recognized that the isopropyl oxide repeating groups may also correspond to:

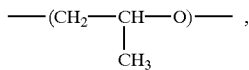

either alone, or in combination with the isomer depicted in Formula IV.

Polyethylene Glycol Derivatives of Glycerides

Suitable polyethylene glycol derivatives of glycerides include any polyethylene glycol derivative of glycerides which are water-soluble and which are suitable for use in a hair care composition. Suitable polyethylene glycol derivatives of glycerides for use herein include derivatives of mono-, di- and tri-glycerides and mixtures thereof.

One class of polyethylene glycol derivatives of glycerides suitable herein are those which conform to the general formula (I):

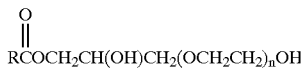

wherein n, the degree of ethoxylation, is from about 4 to about 200, preferably from about 5 to about 150, more preferably from about 20 to about 120, and wherein R comprises an aliphatic radical having from about 5 to about 25 carbon atoms, preferably from about 7 to about 20 carbon atoms.

Suitable polyethylene glycol derivatives of glycerides can be polyethylene glycol derivatives of hydrogenated castor oil. For example, PEG-20 hydrogenated castor oil, PEG-30 hydrogenated castor oil, PEG-40 hydrogenated castor oil, PEG45 hydrogenated castor oil, PEG-50 hydrogenated castor oil, PEG-54 hydrogenated castor oil, PEG-55 hydrogenated castor oil, PEG-60 hydrogenated castor oil, PEG-80 hydrogenated castor oil, and PEG-100 hydrogenated castor oil. Preferred for use in the compositions herein is PEG-60 hydrogenated castor oil.

Other suitable polyethylene glycol derivatives of glycerides can be polyethylene glycol derivatives of stearic acid. For example, PEG-30 stearate, PEG-40 stearate, PEG-50 stearate, PEG-75 stearate, PEG-90 stearate, PEG-100 stearate, PEG-120 stearate, and PEG-150 stearate. Preferred for use in the compositions herein is PEG60 Hydrogenated castor oil.

Water

The compositions of the present invention will also generally contain water. When present water will generally comprise from about 25% to about 99%, preferably from about 50% to about 98%, more preferably from about 65% to about 95%, by weight, of the total composition.

Additional Components

The compositions herein can contain a variety of other optional components suitable for rendering such compositions more cosmetically or aesthetically acceptable or to provide them with additional usage benefits. Such conventional optional ingredients are well-known to those skilled in the art.

A wide variety of additional ingredients can be formulated into the present composition. These include: other hair conditioning ingredients such as panthenol, panthetine, pantotheine, panthenyl ethyl ether, and combinations thereof; other solvents such as hexylene glycol; hair-hold polymers such as those described in WO-A-94/08557, herein incorporated by reference; detersive surfactants such as anionic, nonionic, amphoteric, and zwitterionic surfactants; additional viscosity modifiers and suspending agents such as xanthan gum, guar gum, hydroxyethyl cellulose, triethanolamine, methyl cellulose, starch and starch derivatives; viscosity modifiers such as methanolamides of long chain fatty acids such as cocomonoethanol amide; crystalline suspending agents; pearlescent aids such as ethylene glycol distearate; opacifiers such as polystyrene; preservatives such as phenoxyethanol, benzyl alcohol, methyl paraben, propyl paraben, imidazolidinyl urea and the hydantoins; polyvinyl alcohol; ethyl alcohol; pH adjusting agents, such as lactic acid, citric acid, sodium citrate, succinic acid, phosphoric acid, sodium hydroxide, sodium carbonate; salts, in general, such as potassium acetate and sodium chloride; colouring agents, such as any of the FD&C or D&C dyes; hair oxidising (bleaching) agents, such as hydrogen peroxide, perborate and persulfate salts; hair reducing agents, such as the thioglycolates; perfumes; sequestering agents, such as tetrasodium ethylenediamine tetra-acetate; anti-dandruff agents such as zinc pyrithione (ZPT), sulfur, selenium sulfide, coal tar, piroctone olamine, ketoconazole, climbazole, salicylic acid; antioxidants/ultra violet filtering agents such as octyl methoxycinnamate, benzophenone-3 and DL-alpha tocopherol acetate and polymer plasticizing agents, such as glycerine, diisobutyl adipate, butyl stearate, and propylene glycol. Such optional ingredients generally are used individually at levels from about 0.001% to about 10.0%, preferably from about 0.01% to about 5.0% by weight of the composition.

Product Forms

The hair care compositions of the present invention can be formulated in a wide variety of product forms, including but not limited to creams, gels, aerosol or non-aerosol foams, mousses and sprays. Mousses, foams and sprays can be formulated with propellants such as propane, butane, pentane, dimethylether, hydrofluorocarbon, $CO_2$, $N_2O$, or without specifically added propellants (using air as the propellant in a pump spray or pump foamer package).

Method of Use

The hair care compositions of the present invention may be used in a conventional manner for care of human hair. An effective amount of the composition, typically from about 1 gram to about 50 grams, preferably from about 1 gram to about 20 grams, is applied to the hair. Application of the composition typically includes working the composition through the hair, generally with the hands and fingers, or with a suitable implement such as a comb or brush, to ensure good coverage. The composition is then left on the hair, generally until the consumer next washes their hair.

The preferred method of treating the hair therefore comprises the steps of:

(a) applying an effective amount of the hair care composition to wet, damp or dry hair, (b) working the hair care composition into the hair with hands and fingers or with a suitable implement.

The method can, optionally, comprise a further step of rinsing the hair with water.

EXAMPLES

The following examples further illustrate the preferred embodiments within the scope of the present invention. The examples are given solely for the purposes of illustration and are not to be construed as limitations of the present invention as many variations of the invention are possible without departing from its spirit or scope. All ingredients are expressed on a weight percentage of the active ingredient.

Examples I–III(%wt)

| Ingredient | I | II | III | |
|---|---|---|---|---|
| Water | to 100 | to 100 | to 100 | — |
| cetyl hydroxyethylcellulose[1] | 0.35 | — | 0.20 | A |
| PEG150stearyl/SMDI copolymer[2] | — | 0.40 | — | B |
| methyl paraben | 0.30 | 0.30 | 0.30 | B |
| propyl paraben | 0.15 | 0.15 | 0.15 | B |
| Cetyl alcohol[3] | 0.90 | 0.90 | 1.20 | B |
| Stearyl alcohol[4] | 0.60 | 0.60 | 0.80 | B |
| Cetrimmonium chloride[5] | 0.40 | 0.40 | 0.50 | B |
| PEG 60 hydrogenated castor oil[6] | 0.20 | 0.20 | 0.20 | B |
| DMDM hydantoin | 0.05 | 0.05 | 0.05 | C |
| tetra sodium EDTA | 0.30 | 0.30 | 0.30 | C |
| citric acid | 0.05 | 0.05 | 0.05 | C |
| Perfume | 0.40 | 0.40 | 0.40 | C |

[1]Natrosol 330 C Plus supplied by Aqualon Co.
[2]Aculyn 46 supplied by ISP Co.
[3]Crodacol C-95 supplied by Croda Inc.
[4]Crodacol S-95 supplied by Croda Inc.
[5]Dehyquat ACA supplied by Henkel
[6]Cremophor RH-60 supplied by BASF Ingredient A (if included) is solubilized in water and then heated to 80° C. Ingredients B are added to the hot mixture which is then stirred until homogenous, and cooled to 30° C. through a plate heat exchanger. The cooling rate is maintained at between 0.7 and 1.5° C./min. All of ingredients C are then added. This mixture is then stirred until homogenous.

Examples IV–VI (%wt)

| Ingredient | IV | V | VI | |
|---|---|---|---|---|
| Water | to 100 | to 100 | to 100 | — |
| cetyl hydroxyethylcellulose[1] | 0.35 | — | 0.15 | A |
| PEG150stearyl/SMDI copolymer[2] | — | 0.40 | — | B |
| methyl paraben | 0.30 | 0.30 | 0.50 | B |
| propyl paraben | 0.15 | 0.15 | 0.40 | B |
| Cetyl alcohol[3] | 0.90 | 0.90 | 1.20 | B |
| Stearyl alcohol[4] | 0.60 | 0.60 | 0.80 | B |
| Cetrimmonium chloride[5] | 0.40 | 0.40 | 0.50 | B |
| PEG 60 hydrogenated castor oil[6] | 0.20 | 0.20 | 0.20 | B |
| Cationic Polymer of hydroxyethyl cellulose[7] | 0.10 | 0.20 | 0.35 | A |
| DMDM hydantoin | 0.05 | 0.05 | 0.05 | C |
| tetra sodium EDTA | 0.30 | 0.30 | 0.30 | C |
| citrid acid | 0.05 | 0.05 | 0.05 | C |
| Perfume | 0.40 | 0.40 | 0.40 | C |

[1]Natrosol 330 C Plus supplied by Aqualon Co.
[2]Aculyn 46 supplied by ISP Co.
[3]Crodacol C-95 supplied by Croda Inc.
[4]Crodacol S-95 supplied by Croda Inc.
[5]Dehyquat ACA supplied by Henkel
[6]Cremophor RH-60 supplied by BASF
[7]Polymer having charge density of 1.93 meq/g and wt average mol. Wt of 1.25 million. Available from Amerchol.

Ingredients A (if included) are solubilized in water and then heated to 80° C. Ingredients B are added to the hot mixture which is then stirred until homogenous, and cooled to 30° C. through a plate heat exchanger. The cooling rate is maintained at between 0.7 and 1.5° C./min. All of ingredients C are then added. This mixture is then stirred until homogenous.

Examples VII–IX (%wt)

| Ingredient | VII | VIII | IX | |
|---|---|---|---|---|
| Water | to 100 | to 100 | to 100 | — |
| cetyl hydroxyethylcellulose[1] | 0.35 | — | 0.15 | A |
| PEG150stearyl/SMDI copolymer[2] | — | 0.40 | — | B |
| methyl paraben | 0.30 | 0.30 | 0.50 | B |
| propyl paraben | 0.15 | 0.15 | 0.40 | B |
| Cetyl alcohol[3] | 0.90 | 0.90 | 1.20 | B |
| Stearyl alcohol[4] | 0.60 | 0.60 | 0.80 | B |
| Cetrimmonium chloride[5] | 0.40 | 0.40 | 0.50 | B |
| PEG 60 hydrogenated castor oil[6] | 0.20 | 0.20 | 0.20 | B |
| Phenylpropyldimethyl/trimethylsiloxysicate[7] | 0.10 | 0.30 | 0.20 | C |
| DMDM hydantoin | 0.05 | 0.05 | 0.05 | C |
| tetra sodium EDTA | 0.30 | 0.30 | 0.30 | C |
| citric acid | 0.05 | 0.05 | 0.05 | C |
| Perfume | 0.40 | 0.40 | 0.40 | C |

[1]Natrosol 330 CS supplied by Aqualon Co.
[2]Aculyn 46 supplied by ISP Co.
[3]Crodacol C-95 supplied by Croda Inc.
[4]Crodacol S-95 supplied by Croda Inc.
[5]Dehyquat ACA supplied by Henkel
[6]Cremophor RH-60 supplied by BASF
[7]Baysilone CF 1301 available from GE/Bayer Ingredient A (if included) is solubilized in water and then heated to 80° C. Ingredients B are added to the hot mixture which is then stirred until homogenous, and cooled to 30° C.

through a plate heat exchanger. The cooling rate is maintained at between 0.7 and 1.5° C./min. All of ingredients C are then added. This mixture is then stirred until homogenous.

Examples X–XIII (%wt)

| Ingredient | X | XI | XII | XIII | |
|---|---|---|---|---|---|
| Water | qs | qs | qs | — | |
| cetyl hydroxyethylcellulose[1] | 0.35 | — | 0.15 | 0.20 | A |
| PEG150stearyl/SMDI copolymer[2] | — | 0.40 | — | 0.20 | B |
| methyl paraben | 0.30 | 0.30 | 0.50 | 0.50 | B |
| propyl paraben | 0.15 | 0.15 | 0.40 | 0.40 | B |
| Cetyl alcohol[3] | 0.90 | 0.90 | 1.20 | 1.20 | B |
| stearyl alcohol[4] | 0.60 | 0.60 | 0.80 | 0.80 | B |
| Cetrimmonium chloride[5] | 0.40 | 0.40 | 0.50 | 0.50 | B |
| PEG 60 hydrogenated castor oil[6] | 0.20 | 0.20 | 0.20 | 0.20 | B |
| Cationic Polymer of hydroxyethyl cellulose[7] | 0.35 | 0.20 | 0.30 | 0.30 | A |
| Phenylpropyldimethyl/trimethylsiloxysicate[8] | 0.10 | 0.30 | 0.20 | 0.20 | C |
| DMDM hydantoin | 0.05 | 0.05 | 0.05 | 0.05 | C |
| tetra sodium EDTA | 0.30 | 0.30 | 0.30 | 0.30 | C |
| citric acid | 0.05 | 0.05 | 0.05 | 0.05 | C |
| Perfume | 0.40 | 0.40 | 0.40 | 0.40 | C |

[1]Natrosol 330 C Plus supplied by Aqualon Co.
[2]Aculyn 46 supplied by ISP Co.
[3]Crodacol C-95 supplied by Croda Inc.
[4]Crodacol S-95 supplied by Croda Inc.
[5]Dehyquat ACA supplied by Henkel
[6]Cremophor RH-60 supplied by BASF
[7]Polymer having charge density of 1.93 meq/g and wt average mol. Wt of 1.25 million. Available from Amerchol.
[8]Baysilone CF 1301 available from GE/Bayer.

Ingredients A (if included) are solubilized in water and then heated to 80° C. Ingredients B are added to the hot mixture which is then stirred until homogenous, and cooled to 30° C. through a plate heat exchanger. The cooling rate is maintained at between 0.7 and 1.5° C./min. All of ingredients C are then added. This mixture is then stirred until homogenous.

What is claimed is:

1. A hair treatment composition comprising:
   (a) at least one associative polymer;
   (b) at least one long chain alcohol;
   (c) at least one cationic surfactant;
   wherein the weight ratio of (b):(c) is greater than about 1.5:1.

2. A composition according to claim 1 wherein the weight ratio of (b):(c) is at least about 2:1.

3. A composition according to claim 1 wherein the associative polymer is selected from hydrophobically modified hydroxyalkyl cellulose polymers and hydrophobically modified alkoxylated urethane polymers and mixtures thereof.

4. A composition according to claim 1 wherein the associative polymer is selected from hydrophobically modified hydroxyalkyl cellulose polymers and mixtures thereof.

5. A composition according to claim 1 wherein the total level of associative polymer is from about 0.001% to about 15%.

6. A composition according to claim 1 wherein the total level of long chain alcohols is from about 0.1% to about 20% by weight of total composition.

7. A composition according to claim 1 wherein the long chain alcohol is selected from alcohols with a $C_{10}$ to $C_{22}$ chain and mixtures thereof.

8. A composition according to claim 1 wherein the cationic surfactant is cetyl trimethyl ammonium chloride, stearyl trimethyl ammonium chloride, tetradecyltrimethly ammonium chloride, dicetyldimethyl ammonium chloride, dicocodimethyl ammonium chloride.

9. A composition according to claim 1 wherein the total level of cationic surfactant is from about 0.1% to about 10% by weight of total composition.

10. A method of treatment for hair or skin using the composition according to claim 1.

11. A cosmetic treatment comprising applying a composition according to claim 1 to hair or skin.

* * * * *

UNITED STATES PATENT AND TRADEMARK OFFICE
CERTIFICATE OF CORRECTION

PATENT NO.   : 6,589,517 B1
DATED         : July 8, 2003
INVENTOR(S)  : McKelvey, Graham Neil et al.

It is certified that error appears in the above-identified patent and that said Letters Patent is hereby corrected as shown below:

<u>Title page,</u>
Item [*] Notice, should read -- This patent is subject to a terminal disclaimer --.

Item [57], ABSTRACT,
Line 5, "greater about" should read -- greater than about --.
Line 8, "white" should read -- while --.

Signed and Sealed this

Thirtieth Day of September, 2003

JAMES E. ROGAN
*Director of the United States Patent and Trademark Office*